United States Patent [19]

Beaupied

[11] Patent Number: 4,888,006
[45] Date of Patent: Dec. 19, 1989

[54] GARMENT TO HOLD A OSTOMY APPLIANCE

[76] Inventor: Dolores Y. Beaupied, 200 Inwood Dr., Apt. 106, Wheeling, Ill. 60090

[21] Appl. No.: 151,330

[22] Filed: Feb. 2, 1988

[51] Int. Cl.⁴ ............................................. A61F 5/44
[52] U.S. Cl. ................................. 604/345; 604/343; 2/406
[58] Field of Search ................. 604/332–345; 2/401, 405, 406, 250; 450/150

[56] References Cited

U.S. PATENT DOCUMENTS

| | | | |
|---|---|---|---|
| 2,062,161 | 11/1936 | Chatfield | 2/405 |
| 3,421,505 | 1/1969 | Freeman et al. | 604/345 |
| 3,468,310 | 9/1969 | Kimball | 604/345 |
| 3,844,282 | 10/1974 | King | 2/405 |
| 4,495,662 | 1/1985 | Miller | 604/332 |

*Primary Examiner*—Jerome L. Kruter
*Attorney, Agent, or Firm*—Wallenstein, Wagner & Hattis, Ltd.

[57] ABSTRACT

An ostomy garment comprises an undergarment having front, back and crotch panels, waist and leg bands stitched together to construct a typical panty or undergarment. The garment incorporates a retaining pocket and closure device. The retaining pocket has an opening defined by a crisscross arrangement which surrounds the connected flanges of an appliance and contains the appliance pouch apart from the user's abdomen.

7 Claims, 3 Drawing Sheets

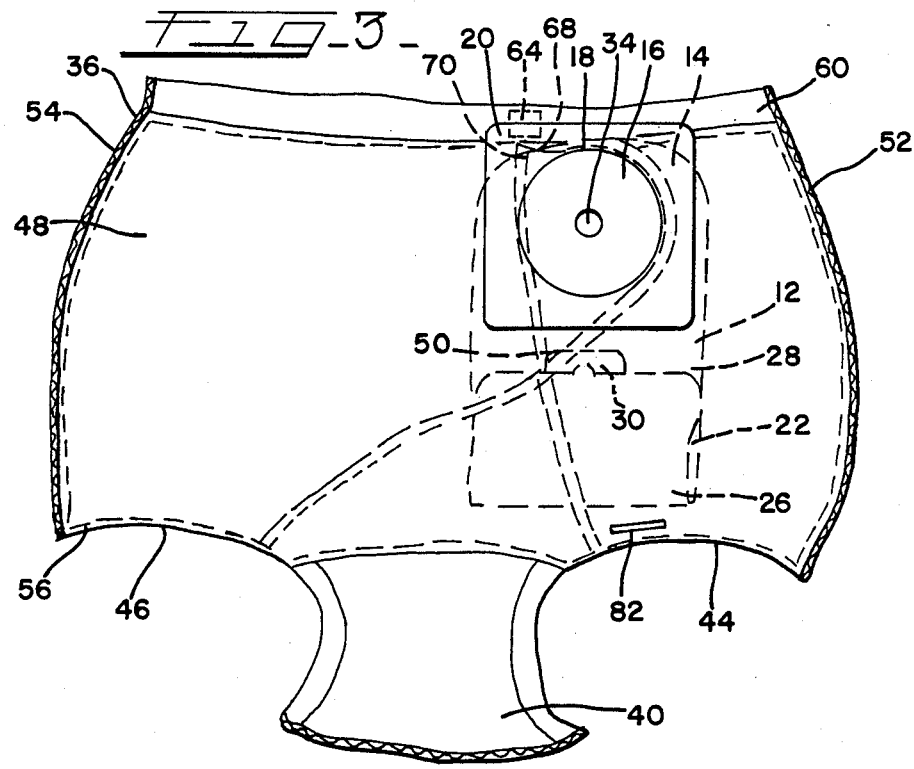
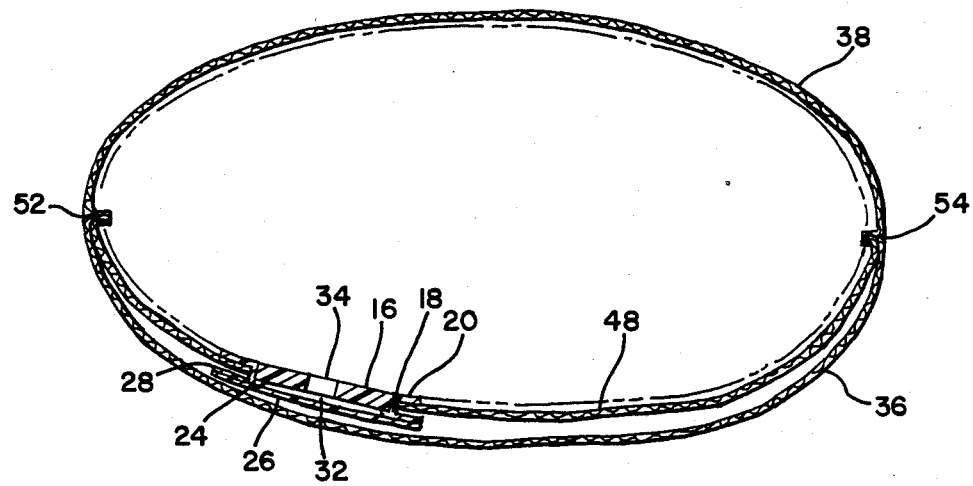

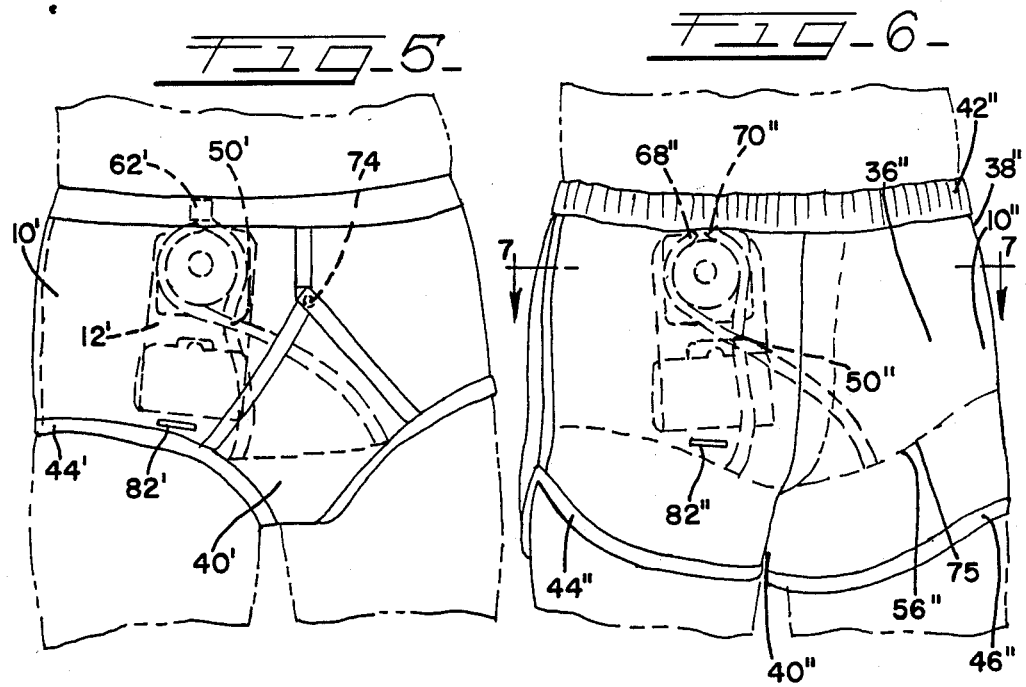
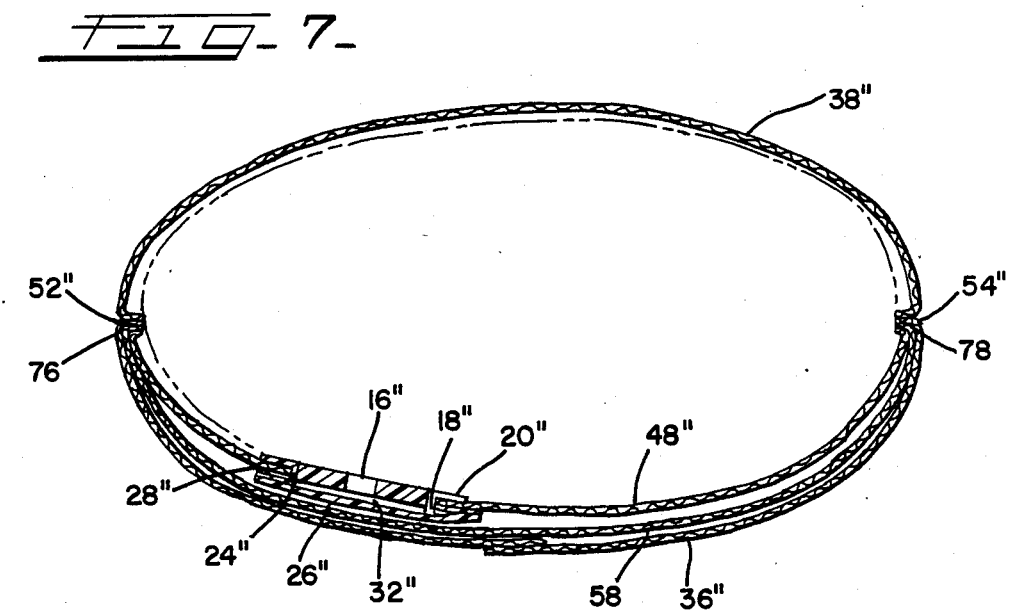

GARMENT TO HOLD A OSTOMY APPLIANCE

TECHNICAL FIELD

The present invention generally relates to ostomy garments worn by individuals required to use one or more ostomy appliances.

BACKGROUND OF THE INVENTION

Individuals can undergo a variety of surgical procedures, where portions of the intestinal and/or urinary tract are removed, the remaining portions are brought to the abdominal wall and a stoma is surgically constructed through which urine or feces will pass. The location and size of the stoma varies from individual to individual as a result of the surgical procedure followed. For example, the location of a stoma created during a colostomy can vary according to the portion of the colon which is diseased. Further, individuals having undergone one ostomy surgery may require additional surgery, resulting in more than one stoma.

After surgery, such individuals typically rely on the use of an ostomy appliance for the collection and disposal of urine and/or feces discharged through the stoma. Again, due to the individual characteristics of the surgical procedures and the created stomas, ostomy appliances vary to meet the differing needs of the user. Typically, ostomy appliances are one or two interlocking pieces which adhere to the user's abdomen, encircling the stoma. In addition to providing for the sanitary reception of material discharged through the stoma, some appliances further allow for drainage of fluid without the complete removal of the appliance.

Individuals having been fitted with an ostomy appliance have typically depended upon an encircling belt or undergarments for support of the appliance. Generally, however, these prior ostomy undergarments have failed to provide sufficient support of the appliance necessary for the comfort of the user. Often maintenance of the appliance by the user is difficult and awkward when worn with prior garments, or containment articles. With prior garments, the appliance was readily noticeable under the user's clothing. Further, prior garments and containment articles made either no provision or insufficient accommodations for night and intimate wear by the user. For example, a prior appliance was developed to fit each individual by creating molds or impressions of the user's body in two positions, standing erect and reclining. These numerous insufficiencies of the prior garments or articles have adversely affected both the physical and psychological comforts and needs of the user.

One object of the present invention is to provide an ostomy garment which is readily adaptable to the various needs of the user, the location and size of the stoma and the appliance fitted for the user. Through this adaptability, the present invention provides support for a user of at least one ostomy appliance while providing comfort and convenience irrespective of the user's position or activities. By caring for the physical needs of support, containment, comfort and nonperceptibility, the psychological effect on the user is one of improved confidence and self image.

SUMMARY OF THE INVENTION

According to the present invention, a new ostomy garment has been developed which can retain and support one or two ostomy appliances, irrespective of the size of the appliance, the location of the stoma, or the activities of the user.

The present invention provides an improved retaining means for an ostomy appliance while permitting easy access to the appliance for maintenance purposes. The ostomy garment of the present invention also provides for the comfort and convenience of the user as it is adaptable to various appliances and various physical and sexual activities of the user. Further, a moisture barrier between the abdomen of the user and the appliance is provided for the added comfort of the user.

The garment of the present invention provides support and comfort while being nonperceptible through an outer garment of the user, unlike prior ostomy garments, thus improving the self-image of the user.

More specifically, the present invention for users of ostomy appliances is comprised of an undergarment having a retaining pocket with an opening of a criss-cross arrangement which securely surrounds the flange member of the appliance and allows the pouch member of the appliance to pass through.

BRIEF DESCRIPTION OF THE DRAWINGS

FIG. 3 is an elevation view of the ostomy garment taken from the inside of the garment and substantially in the plane of the line 3—3 of FIG. 1;

FIG. 4 is a cross-sectional view of the ostomy garment substantially in the plane of the line 4—4 of FIG. 1;

FIG. 5 is a perspective view of the ostomy garment of the preferred embodiment of the invention as worn by a male user of an ostomy appliance;

FIG. 6 is a perspective view of the ostomy garment of another embodiment of the invention as worn be a male user of an ostomy appliance; and FIG. 7 is a cross-sectional view of the ostomy garment substantially in the plane of the line 7—7 of FIG. 6.

DETAILED DESCRIPTION OF THE PREFERRED EMBODIMENT

Figure 1:
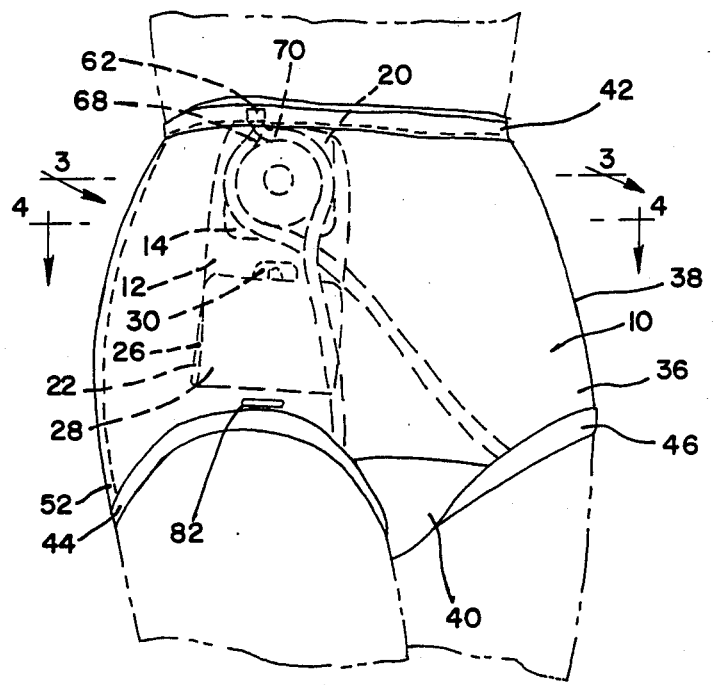
FIG. 1 is a perspective view of the ostomy garment of the preferred embodiment of the invention as worn by a female user of an ostomy appliance.
Figure 2:
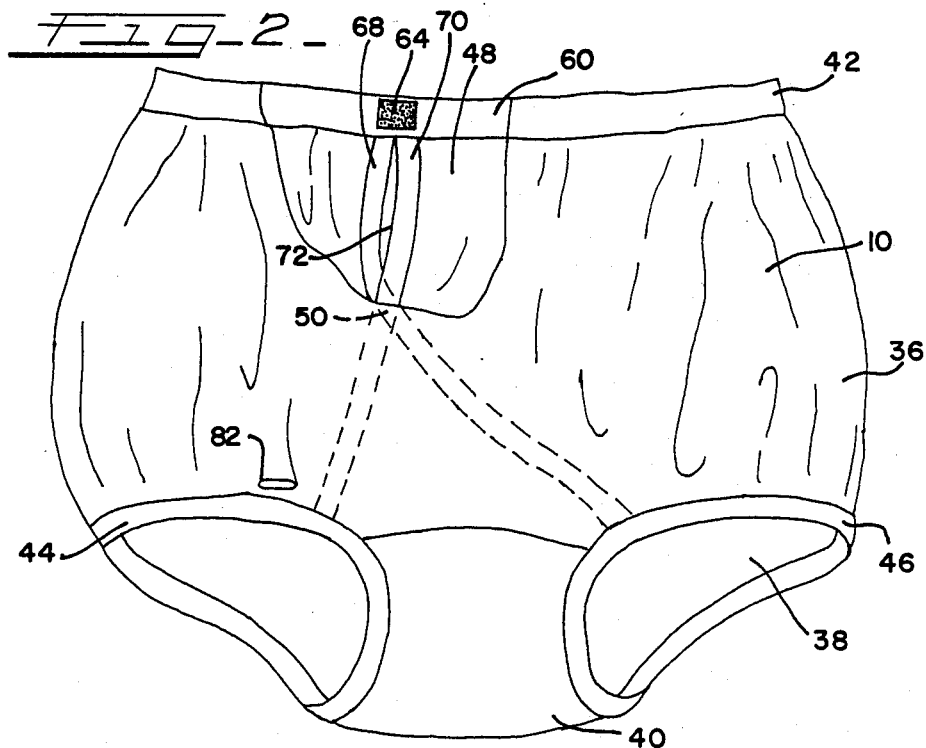
FIG. 2 is a front elevation view of the ostomy garment shown in FIG. 1, partly broken away, omitting the ostomy appliance.

While this invention is susceptible of embodiment in many different forms, there is shown in the drawings and will herin be described in detail a preferred embodiment of the invention with the understanding that the present disclosure is to be considered as an exemplification of the principles of the invention and is not intended to limt the broad aspect of the invention to embodiment illustrated.

Referring to the drawings, FIG. 1 discloses an ostomy garment worn by a female user of one, two piece ostomy appliance 12 and constructed in accordance with the present invention generally referenced by 10. The ostomy appliance 12 generally comprises of a wafer or apron 14 having a disc 16 fused with a circular wafer flange 18 which outer circumference is covered with an adhesive skin barrier portion 20 and a pouch 22 having a circular pouch flange 24 and two side walls 26, 28 fused together, leaving an opening 30 distally positioned from the wafer which can be closed off with closures, clamps or irrigation valves.

Opposed to pouch opening 30, facing the user's abdomen, the pouch flange 24 surrounds an opening 32 in side wall 28. Secured on the abdomen of the user by adhesive barrier 20, the disc opening 34 receives the user's stoma and allows wafer flange 18 to extend away from the user's abdomen. Having compatible interlocking features, wafer flange 18 connects with the corresponding pouch flange 24. While a two piece ostomy appliance is referenced by the drawings, the disclosed invention can accommodate one or two piece appliances or "closed" appliances which do not provide for the distal opening 30 as referred herein.

Generally, ostomy garment 10 has front and back panels 36, 38, a crotch panel 40 and a waist band 42 stitched together to construct a typical panty or undergarment. As shown in FIGS. 1 and 5, the ostomy garment has leg bands 44, 46 which can either hug the wearer's legs or flare as shown in FIG. 6. As can be readily visualized, the crotch panel 40 of the female garment can be provided with a slit to permit a female user to be sexually active without disturbance to the appliance 12. Also, releasable fasteners could be used to secure the crotch panel to the front panel.

A retaining pocket 48 is interposed between front panel 36 of garment 10 and abdomen of the user. Retaining pocket 48 is of a crisscross arrangement 50 over the abdomen of the user with side seams 52, 54 of the garment 10 joining the outer sides of pocket 48 with front panel 36 of garment 10. The crisscross arrangement defines an opening through which the appliance flanges 18, 24 extends, and will be described hereinafter.

The lower edge 56 of retaining pocket 48 is stitched to the leg bands 44, 46 and crotch panel 40 of the garment 10, as shown in FIG. 3. The waist band 60 of retaining pocket 48 is stitched to garment waist band 42 at the corresponding seams 52, 54 of the garment. Corresponding members 62, 64 of a fastener or closure device 66 are positioned on waist band members 42, 60 proximate to the attachment of finished edges 68, 70 of the crisscross arrangement 50 to the waist band 60.

The crisscross arrangement 50 of retaining pocket 48 is created by finished edges 68, 70 which are positioned off-center relative to front panel 36 of the garment 10. In this off-center position, finished edges 68, 70 are stitched adjacent to one another with pocket waist band 60. Preferably, finished edges 68, 70 are in juxtaposed abutting relation to each other, but could be slightly spaced, if desired, when stitched with pocket waist band 60. The finished edges 68, 70 extend to the lower edge 56 of retaining pocket 48 with edge 68 being stitched with leg band 46 and, similarly, edge 70 with band 44. Being parallel at point edges 68, 70 are joined at band 60 and opposed at pocket edges 68, 70 are joined with bands 48, 44, finished edges 68, 70 overlap to define an adjustable, elongated, slanted slot 72 which extends across retaining pocket 48.

When wearing ostomy garment 10 with appliance 12, finished edges 68, 70 adjust and securely surround interlocked wafer flange 18 and pouch flange 24, allowing pouch 22 to pass through slot 72, to be retained by pocket 48. With edges 68, 70 surrounding flanges 18 and 24, retaining pocket 48 is positioned between pouch 22 and the abdomen of the user, acting as a moisture barrier for the comfort of the user. While retaining pocket 48 is preferably of a cotton or cotton blend fabric, other barrier materials may be used.

Convenient access to pouch 22 is provided by unfastening closure device 66 while garment 10 is being worn by the user, to facilitate maintenance of the appliance 12. Worn in this manner, retaining pocket 48 also provides a barrier between adhesive barrier 20 and pouch 22. Further, the secure surrounding of flanges 10, 24 by the crisscross arrangement 50 and the containment of pouch 22 by retaining pocket 48 provide sufficient support for appliance 12 regardless of the position or activity of the user.

Referring to FIG. 5, a brief 10' can be adapted to the present invention. The brief 10' can be provided with an additional closure device 74 on front panel 36' to permit the triangle-shaped portion of front panel 36' to be folded toward the user's body and crotch panel 40', thereby allowing access to the penis without disturbance to the appliance 12'.

An additional embodiment of the present invention can be adapted to a boxer style brief 10'', as shown in FIG. 6. Shown as worn by a male user of one, two piece ostomy appliance 12 the construction of which has been previously described, boxer style garment 10'' is of a typical construction having front and back panels 3'', 38'', a crotch panel 40'', a waist band 42'' and leg bands 44'', 46''.

A retaining pocket 48'' having a crisscross arrangement 50'' is interposed between front panel 36'' and the user's abdomen similar to pocket 48. Rather than stitch the lower edge 56'' of retaining pocket 48'' to leg bands 44'', 46'' and crotch panel 40'', thereby restricting the activities a male wearer, lower edge 56'' is stitched to a corresponding edge 75 of an insert panel 58. Interposed between front panel 36'' and retaining pocket 48'', insert panel 58 has side edges 76, 78 stitched with seams 52'' and 54'', respectively and an upper edge 80 stitched with waist band 42'' of garment 10'' Corresponding members 62'', 64'' of a fastener or closure device 66'' are positioned on edge 80 and pocket waist band 60'' proximate to the off-center attachment of finished edges 68'' and 70'' of crisscross arrangement 50'' to waist band 60''.

When wearing ostomy garment 10 with appliance 12'', the crisscross arrangement 50'' of retaining pocket 48'' similarly provides for the secure surrounding of flanges 18'' and 24'' while pouch 22'' passes through slot 72''. Once through slot 72'', pouch 24'' is retained between pocket 48'' and insert panel 58 without restricting the position or activity of the male user.

Further, ostomy garments 10, 10', 10'' can be provided with a slit 82, 82', 82'' in front panel 36, 36', 36'' respectively to permit passage of a catheter.

In addition, ostomy garments 10, 10', 10'' can be worn in conjunction with an ostomy appliance provided with or used with a belt device which encircles the user's trunk. When worn with such a belt device, neither the belt nor the present invention require any adaption.

While specific embodiments have been illustrated and described, numerous modifications come to mind without significantly departing from the spirit of the invention, and the scope of the accompanying claims.

What I claim is:

1. An undergarment for supporting an ostomy appliance having a flange member comprising:

front, back and crotch panels interconnected to form the garment;

a retaining pocket interposed between said panels and connected to one of said panels with an ostomy appliance received into said pocket, said retaining pocket having an opening defined by a criss-cross arrangement means of a front and back panel formed by adjacent overlapping edges with said opening adapted to receive a flange of an ostomy appliance therethrough, said overlapping edges accommodating a flange member of an ostomy appliance at different positions of a user's body.

2. The undergarment described in claim 1, wherein said retaining pocket defines a barrier between the appliance pouch and the user.

3. The undergarment described in claim 1, wherein said retaining pouch comprising a panel means defining an adjustable, elongated, slanted slot crossing over the abdomen of the user, side seams stitched with adjacent side seams of the undergarment, a waist band stitched with adjacent side seams of the undergarment closure member corresponding to a closure receiving member on the undergarment waist band, and a lower edge stitched to adjacent leg bands and crotch panel of the undergarment.

4. The undergarment described in claim 1, wherein said retaining pouch comprising a panel means having two panels, one panel having said crisscross arrangement and defining an adjustable, elongated, slanted slot crossing over the abdomen of the user, side seams stitched with adjacent side seams of the garment, a waist band stitched with adjacent side seams of the undergarment, a closure member corresponding to a closure receiving member on the undergarment waist band, and a lower edge stitched to adjacent lower edge of a second insert panel.

5. The undergarment described in claim 1, wherein said opening is defines by said criss-cross arrangement comprises overlapping edges defining an adjustable, elongated, slanted slot.

6. An undergarment for supporting an ostomy appliance having a connecting flange comprising:
front, back and crotch panels, waist band and leg bands;
a retaining pocket of pliable fabric interposed as a barrier between said front panel and abdomen of wearer, said pocket having outer side edges, a lower edge joined with said undergarment, and a waist band adjacent to said garment waist band;
an appliance support means integrally formed with said retaining pocket and having an opening defined by a criss-cross arrangement means of a front and back panel formed by overlapping edges defining an adjustable, elongated, slanted slot for surrounding a flange means of an ostomy appliance with one end of said edge being secured to said pocket waist band off-center of said front panel and overlapping with said garment waist band; and,
a closure device having corresponding adjacent members on said garment waist band and pocket waist band, proximate to said criss-cross edges for attachment on said pocket waist band.

7. An undergarment for supporting an ostomy appliance having a connecting flange comprising:
front, back and crotch panels, waist band and leg bands;
a retaining pocket of pliable fabric interposed as a barrier between said front panel and abdomen of a wearer, said pocket having an insert panel and second panel with outer side edges of both panels joined with said undergarment, lower edges of both panels stitched together with said insert panel stitched to said waist band and said second panel having a waist band adjacent to said garment waist band;
an appliance support means integrally formed with said retaining pocket and having an opening defined in said second panel by a criss-cross arrangement of overlapping edges defining an adjustable, elongated, slanted slot for surrounding a flange means of an ostomy appliance; and,
a closure device having corresponding adjacent members on said garment waist band and pocket waist band proximate to said criss-cross edges for attachment on said pocket waist band.

* * * * *